Figure 1:
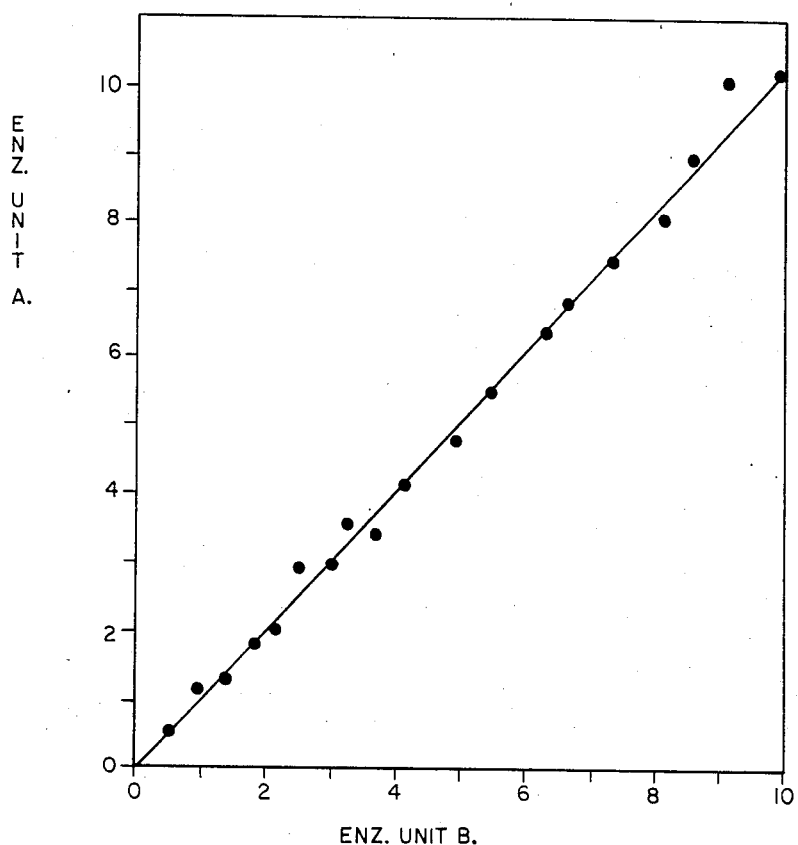

United States Patent [19]

Kinnunen et al.

[11] Patent Number: 4,668,623

[45] Date of Patent: May 26, 1987

[54] METHOD OF FLUOROMETRICALLY MEASURING THE ACTIVITY OF FAT-DEGRADING ENZYMES

[75] Inventors: Paavo K. J. Kinnunen; Tom M. Schroder; Jorma A. Virtanen, all of Espoo, Finland

[73] Assignee: KSV-Chemicals Oy, Finland

[21] Appl. No.: 582,527

[22] Filed: Feb. 22, 1984

Related U.S. Application Data

[63] Continuation-in-part of Ser. No. 251,197, Apr. 6, 1981, abandoned.

[30] Foreign Application Priority Data

| Apr. 9, 1980 | [FI] | Finland | 801117 |
| Apr. 18, 1980 | [FI] | Finland | 801258 |
| Feb. 27, 1981 | [FI] | Finland | 810616 |

[51] Int. Cl.$^4$ ............................................. C12Q 1/44
[52] U.S. Cl. ........................................ 435/19; 435/18; 435/21
[58] Field of Search .............................. 435/18, 19, 21

[56] References Cited

U.S. PATENT DOCUMENTS 4,261,968 4/1981 Ullman et al. ........................ 435/7
4,360,694 11/1982 Kinnunen et al. ................... 560/263

OTHER PUBLICATIONS

Fleisher et al.—Chem. Abst., vol. 75 (1971), p. 105296c.
Taskinen et al.—Clinic Chem. Acta, vol. 104 (1980), pp. 107–117.

*Primary Examiner*—Sam Rosen
*Attorney, Agent, or Firm*—Wolf, Greenfield & Sacks

[57] ABSTRACT

The object of the present invention is a new method for fluorometrically assaying the activity of fat-degrading enzymes, such as lipases and phospholipases in samples containing said enzyme, such as in serum. According to the method the enzyme containing sample is reacted with a substrate containing acyl- or alkylglycerols or -phosphoglycerols having at least one fluorescent group, such as a pyrene group. The compounds may in addition contain flurorescence quenching groups. The enzyme hydrolyzes the substrate thus giving rise to changes in the fluorescence intensity during the enzyme reaction and the changes in the intensity are measured at a specific emission wavelength of the fluorescent group employed. The rate of change of the invensity is proportional to the enzyme activity in the sample.

The invention concerns also the new compounds containing fluorescent groups to be used in the method.

6 Claims, 2 Drawing Figures

DEGRADATION OF RADIOACTIVE (A) AND FLUORESCENT (B) PHOSPHOLIPID IN A PHOSPHOLIPASE $A_2$ REACTION. ENZ. UNIT = ENZYMATIC ACTIVITY, NANOMOLES LYSOPHOSPHOLIPID PER MINUTE AND ml.. THE AMOUNT OF ENZYME USED WAS VARIED AND THE ENZYMATIC ACTIVITY MEASURED WITH BOTH METHODS.

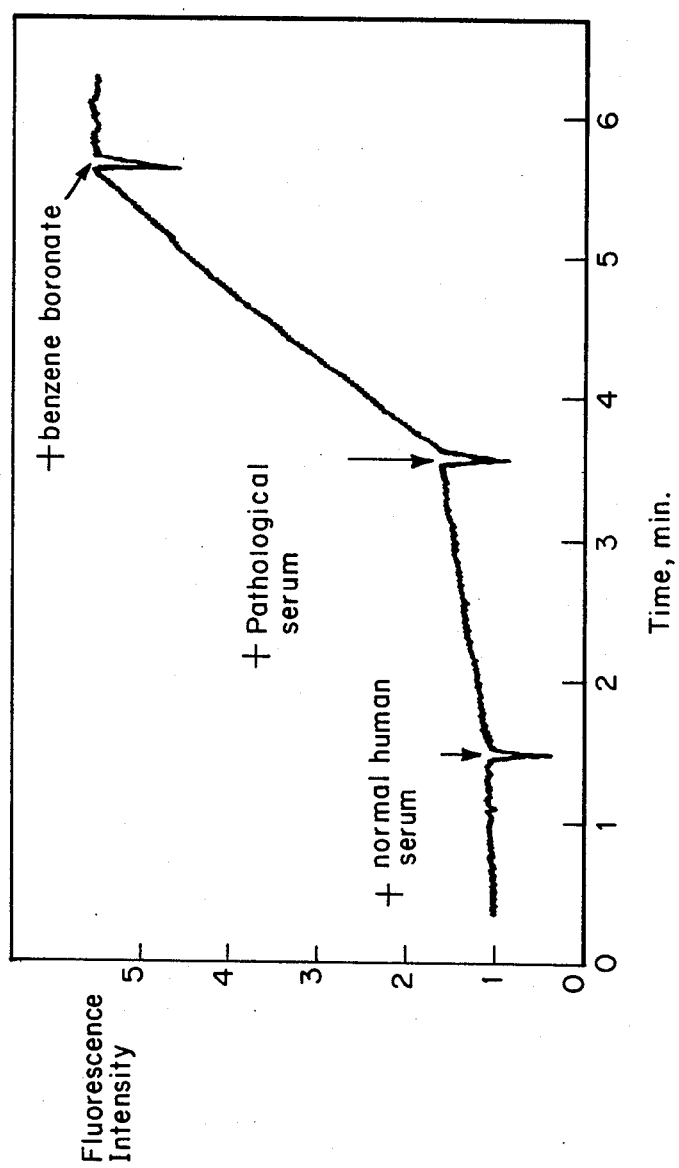

METHOD OF FLUOROMETRICALLY MEASURING THE ACTIVITY OF FAT-DEGRADING ENZYMES

RELATED APPLICATION

This application is a continuation-in-part of U.S. application Ser. No. 251,197 filed Apr. 6, 1981, now abandoned.

The object of the present invention is a clinicoanalytical assay method which is based on changes occurring in the fluorescence intensity. One such method is lipase and phospholipase, especially phospholipase $A_2$ assay in serum. Lipases are enzymes which split triacylglycerols into free fatty acids, glycerides and glycerol. Lipases differ from each other i.a. so to their stereospecificity, and some lipases have the ability to distinguish between the fatty acids in the 1- and 3-positions of an sn-triacyl-glycerol. Phospholipase $A_2$ splits the fatty acid in the 2-position with respect to the phosphoryl group of a phospholipid, the end products being a lysophospholipid and a free fatty acid.

Important from the standpoint of clinical chemistry are the lipase and phospholipase enzymes which under normal conditions are released into the gastro-intestinal tract. I.a. in connection with pancreatitis these enzymes, however, are released into the blood stream and consequently it is of diagnostical importance to measure the enzyme activity in the plasma.

Hitherto two methods for measuring pancreatic lipase in serum have been used. According to the first method, serum is reacted with a triglyceride emulsion whereafter the liberated fatty acids are measured, usually titrimetrically. This method is cumbersome, inexact and its reproducibility poor. Another method used is the nephelometric. According to this method the decrease in the scattering of light as a result of the degradation of the emulsion particles by the lipase is measured, as a function of time. This method is relatively sensitive but not very reproducible. Also the endogenic triglycerides of the serum interfere very strongly with the measurement and it is not possible to make nephelometrically reliable lipase assays from lipemic samples.

The assay methods for phospholipases have been based on the use of a radioactive substrate, whereby e.g. $^{14}C$- or $^3H$-atoms are introduced into the fatty acid in the 2-position and the degree of radioactivity of the fatty acid split by the phospholipase $A_2$ is measured. The method is however cumbersome because of the many stages involved, and it requires special apparatuses, i.a. a scintillation counter.

The object of the present invention is to provide a fluorometric assay method wherein substrates containing glycerol and phosphoglycerol compounds are used, into which compounds fluorescent groups have been introduced, and optionally also quencher groups, and wherein the changes in the fluorescence intensity due to the enzymatic reaction are measured. By means of the method it is possible, without any cumbersome separation steps, to determine for example the lipase and phospholipase activity in a serum sample, which makes the method especially well suited for hospital laboratory use.

The object of the present invention is thus a method for fluorometrically measuring the activity of fatdegrading enzymes in samples containing said enzyme according to which method the enzyme containing sample is combined with a substrate which contains within oil or fat emulsion droplets or micelles and/or liposomes, an acyl- or an acyl-alkyl-glycerol or -phosphoglycerol which reacts with the enzyme to be assayed, wherein at least one of the acyl or alkyl groups contains a fluorescent group and the other groups may optionally contain a fluorescence quenching group, the substrate is excited at the specific excitation wavelength of the fluorescent group in question and the change, due to the enzyme, in the fluorescence intensity of the substrate per time unit is measured at a specific emission wave length of the fluorescent group, the rate of change being directly proportional to the enzyme activity in the sample.

In the method according to the invention compounds are used having the formula

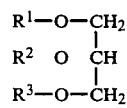

wherein
(a) at least two of the groups $R^1$, $R^2$ and $R^3$ denote a saturated or unsaturated acyl group with 3 to 36 carbon atoms, and the third can denote also hydrogen or a saturated or unsaturated alkyl group with 3 to 36 carbon atoms, or
(b) one of the groups $R^2$ and $R^3$ denotes a phosphoryl group

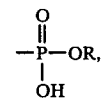

wherein R is hydrogen, ethanolamin, ethylene glycol, choline, glycerol or serine, and the other, as well as $R^1$, denotes an acyl or alkyl group as defined above, provided that the carbon atom in the 2-position to the phosphoryl group may contain only an acyl group, and wherein in the compound of formula I always at least one of the acyl or alkyl groups $R^1$, $R^2$ and $R^3$ is substituted with a fluorescent group, and wherein one or both the other groups may be optionally substituted with a fluorescence quenching group.

The fluorescent group may be pyrene, tetracene, anthracene, phenanthrene, naphthalene, coumarone, coumarin, acridine, benzocarbazone, aminonaphtalenesulfonic acid, mono-, di- or tri-iodo-benzene, perylene, phenyloxadiazole, diphenyloxazole, alloxazine, stilbene, dibenzofuran, fluorene, fluorenone, oxopiperazine, p-quinone, methylumbelliferone, phenazine, phenylindole, quinoline, di-ethylaniline, phenol, diphenylacetylene, benzotiophen, pyrimidine, xanthone, thiocarbocyanide, 1,3,5,7-dekatetra-ene.

A suitable fluorescent group is pyrene because of its well-characterized fluorescence behaviour (Th. Förster, Angew. Chem. 81, 364 (1969) and S. C. Charlton et al, The Journal of Biol. Chem. Vol. 251, No 24, 7952 (1976)).

The fluorescence may be sensitized when using compounds of the formula I containing two fluorescent groups, by introducing into one of them electron donating groups such as methyl, methoxy, hydroxyl or dimethylamino groups, and into the other electron attracting groups, such as cyano and nitro groups.

As a quencher preferably halogen is used, such as bromine, iodine or chlorine, or halogen substituted groups, such as halogen substituted phenyl groups.

A first sub group (a) of the compounds of the formula I comprises for lipase assay suitable triacyl-, diacyl-monoalkyl- and diacyl-glycerols, respectively, wherein at least one of the acyl and alkyl groups is substituted with a fluorescent group, and wherein one other or both the other groups may be substituted with a fluorescence quenching group.

Of these may be mentioned especially the triacyl-glycerols or the formula I wherein one, two or all three acyl groups may contain a fluorescent group, suitably a pyrene group, as well as 1,3-diacyl-2-alkyl-sn-glycerols, which can be substituted with fluorescent groups as the triacyl-glycerols.

Usuable intramolecularly quenched compounds of this group are for example triacyl- or 1,3-diacyl-2-alkyl-sn-glycerols which in their 2-position contain a fluorescent group, whereby the quenching group, suitably a bromine group, is in the 1- and/or 3-position.

The second sub group (b) comprises phospholipid compounds suitable for phospholipase A$_2$ assay and having the formula

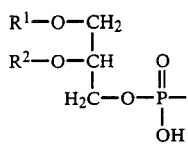 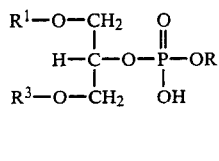

Ia Ib wherein the formula Ia the group R$^2$ and in the formula Ib the group R$^1$ is an afore mentioned acyl group, and wherein at leat one of the groups R$^1$ and R$^2$, or R$^1$ and R$^3$, respectively, contains a fluorescent group, and the other optionally a quenching group.

Of these may be mentioned especially the 1,2-diacyl- or 1-alkyl-2-acyl-compounds of formula Ia, wherein one or both of the groups in the positions 1 and 2 contains a fluorescent group. A suitable compound is also the corresponding compound wherein the fluorescent group has been quenched with a bromine or iodine atom or with some other halogen containing group.

Especially advantageous compounds are the following

I. 1-oleoyl-2-/4-(3-pyrenyl)-buturyl/-3-oleoyl-sn-glycerol
II. 1-(6-bromohexanoyl)-2-/4-(3-pyrenyl)-buturyl/-3-oleoyl-sn-glycerol
III. 1-(4-(3-pyrenyl)-buturyl)-2-(6-bromohexanoyl)-3-oleoyl-sn-glycerol
IV. 1-(4-(2-anthryl)-buturyl)-2-(6-bromohexanoyl)-3-oleoyl-sn-glycerol
V. 1,2-di-(4-(4-pyrenyl)-buturyl)-sn-glycero-sn-3-phosphorylglycerol
VI. 1-(4-(3-pyrenyl)-buturyl)-2-(6-bromohexanoyl)-sn-glycero-3-phosphorylglycerol
VII. 1-(4-(3-pyrenyl)-buturyl)-2-(6-bromohexanoyl)-sn-glycero-3-phosphorylethylenglycol
VII. 1-(hexatriacontanyl)-2-(4-(3-pyrenyl)-buturyl)-sn-glycero-3-phosphorylglycerol
IX. 1-(6-bromohexanoyl)-2-(4-(3-prenyl)-buturyl)-sn-glycero-3-phosphorylcholine
X. 1-(4-(2-anthryl) -buturyl) -2-(6-bromohexanoyl)-sn-glycero-phosphorylglycerol
XI. 1-(10-(2-anthryl)-decanoyl)-2-(10-(3,5-dibrom-4-methoxifenyl)-decanoyl)-sn-glycero-phosphorylglycerol
XII. 1-(10-(2-anthryl)-decanoyl)-3-linoleyl-sn-glycerol-2-phosphorylcholine
XIII. 1-(10-(3-pyrenyl)-decanoyl)-3-(12-bromododecanoyl)-sn-glycerol-2-phosphorylcholine
XIV. 1,2-di-(4-(3-pyrenyl)-buturyl)-sn-glycerol
XV. 1-(4-(3-pyrenyl)-buturyl)-2-(6-bromohexanoyl)-sn-glycerol
XVI. 1-(6-bromohexanoyl)-2-(4-(3-pyrenyl)-buturyl)-sn-glycerol The assay method according to the invention is suitably carried out using an emulsified substrate which in addition to the assay compound contains an oily or fatty substance such as olive oil, lechithin, tributyrin, soya oil, triolein and similar substances well known in the art, in a concentration sufficient to allow the formation in the substrate of micelles and/or liposomes containing the compound, i.e. in a concentration above the critical micellar concentration, which, as known in the art, will be highly dependant on the nature of the substrate. The assay compound molecules will align themselves within the oil particles so that the lipophilic portion of the molecule extends inwards into the micelle or liposome, packing the individual molecules of the assay compound closely together and consequently giving rise to a more pronounced and more accurately measured fluorescence effect.

It is, however, also to be noted that the assay compounds are in themselves fatty substances an thus the same pronounced fluorescence effect can be achieved by using the assay compound as such without the addition of an auxiliary fatty substance. For practical purposes, however, the assay compound is preferably used together with an additional oil or fat, as stated above.

The concentration of the assay compound in the substrate medium can vary over a wide range, but good results have been obtained using a concentration range of approximately 0.05 to 50 micromolar, preferably about 1 to 50 micromolar; within the preferred range one may obtain e.g. intense excimer fluorescence, exceeding the fluorescence due to monomeric species.

When in the method a compound is used which contains a single fluorescent group, such a compound forms, when emulsified in oil, whereby the individual molecules are packed close together, a so-called intermolecular dimer, i.e. an excimer, which, when excited at the excitation wavelength of the fluorescent group in question, fluoresces at the excimer wavelength characteristic for this group. When a substrate containing such a compound is reacted with an enzyme, one obtains through hydrolysis, depending on the enzyme and the compound used, as degradation products free fatty acids as well as mono- or disubstituted glycerols or lysophospholipides, respectively, which leave the emulsion particles whereby the intermolecular interaction between the fluorescent groups disappears and consequently the excimer fluorescence intensity decreases and the intensity of the monomer fluorescence, due to the fluorescent free fatty acid or the fluorescent glycerol product, increases.

For example, the above mentioned compound I, 1-oleoyl-2-(4-(3-pyrenyl)-buturyl) -3-oleoyl-sn-glycerol, forms emulsified in oil, an intermolecular excimer, which, when excited at the excitation wavelength of about 320–345 nm, fluoresces at the excimer wavelength of 470 nm of pyrene. When such an emulsion reacts with pancreatic lipase there is formed, because the pancreatic lipase does not exhibit stereospecificity, two free fatty acids and 2-(4-(3-pyrenyl)-buturyl)-glycerol. As a result of the enzymatic reation the excimer fluorescence intensity decreases and that of the monomer fluorescence correspondingly increases. The change in fluorescence intensity may be followed either at the excimer wavelength of pyrene of ca 470 nm or at its monomer wavelength of ca 390 to 400 nm, and the rate of change of the intensity is directly proportional to the amount of fluorescent compound degraded by the enzyme, i.e. to the enzymatic activity.

A strongly fluorescent intramolecular excimer is formed by compounds of the formula I which in the same molecule contain two or three fluorescent groups. As a result of the enzymatic reaction the interaction between these fluorescent groups gradually disappears, whereby the excimer fluorescence intensity decreases and correspondingly the monomer fluorescence intensity increases. When using for example in the substrate the compound V, 1,2-di-(4-(3-pyrenyl)-buturyl) -sn-glycero-sn-3-phosphorylglycerol, the phospholipase $A_2$ hydrolyzes the fatty acid chain in the 2-position and as reaction products a fluorescent free fatty acid and a fluorescent pyrene-fatty acid phosphatide are formed. As a result of the enzymatic reaction the pyrene excimer fluorescence at the wavelength of about 470 nm weakens and its monomer fluorescence at the wavelength of about 400 nm increases, and the rate of change of the fluorescence intensity is proportional to the degree of hydrolyzis. By following for example at the wavelength of about 470 nm the rate of change of the fluorescence intensity, it is possible to determine the amount of fluorescent compound degraded per time unit, which in turn is dependent on the enzymatic activity.

The enzymatic activity can be measured also by using according to the invention a compound which contains both a fluorescent as well as a group, or groups, preferably bromine atoms, quenching the intramolecular fluorescence. As a result of the enzymatic reaction a fatty acid containing either a fluorescent group or a quenching group is split off and a fluorescent fatty acid or a fluorescent glycerol compound is formed which fluoresces at the monomer wavelength. The increase in intensity, due to a lesser degree of quenching, is enhanced by the same phenomenon as when using a compound containing only one fluorescent group. The method may be carried out also by using an oil-emulsified substrate containing both a compound having one fluorescent group and a compound which contains a fluorescence quenching group. In oil these compounds are forced into close contact thus forming a so-called intramolecularly quenched macromolecule, which as a result of the enzymatic reaction is broken down into products which fluoresce at the monomer wavelength.

In all cases the method is calibrated with solutions containing known amounts of fluorescent compound.

An object of the invention are also the compounds usable for carrying out the method according to the invention, expecially the compounds of formula I, as new substances.

The compounds of the invention may be prepared (M. Kates, Methods in Membrane Biology, Vol. 8, 1977, Plenum Publ. Corp. p. 219–290) for example by introducing into glycerol or especially into D-mannitol the desired acyl and/or alkyl substituents, which optionally contain the desired fluorescent or quencher groups. Thereafter the substituted D-mannitol is split and reduced to the corresponding glycerol. The substituted glycerol thus obtained can further be esterified or etherified in its free position, for example to introduce the phosphoryl group or its derivative in order to prepare the desired compound.

One advantageous mode of preparing 1,2-diacyl-sn-glycerol derivatives is described in the U.S. Pat. No. 4,360,694. Into such a compound the phosphoryl glycerol group may be introduced by reacting 1,2-diacyl-glycerol with phosporoxychloride in the presence of triethylamine. The product obtained is then reacted with 1-trityl-sn-glycerol in the presence of triethylamine and the hydroxy groups of the phosphorylglycerol are liberated. In the publication Eibl. H., Proc. Natl. Acad. Sci., 75 (1978), p. 40–74 are disclosed methods for introducing phosphoryl-ethanolamine and -choline.

The following examples illustrate the invention.

EXAMPLE 1

Phospholipase $A_2$ activity was measured using the following phospholipid substrate which in 2.90 ml contains 1 mM dioleoylphosphatidyl-glycerol
1 nM 1,2-di-(4-(3-pyrenyl)-buturyl)-sn-glycero-sn-3-phosphorylglycerol
2 mM $CaCl_2$
2 mM cholate
50 mM tris-HCl, ph 7.4.

The fluorescence was measured with a Perkin-Elmer-fluorescence-spektrofotometer, excitation opening 3 nm, emission opening 6 nm, excitation wavelength 320 nm, emission wavelength 470 nm. The base level was determined whereafter 100 μl of a sample containing phospholipase $A_2$ from cobra venom was added to the substrate. The decrease in fluorescence intensity was followed as a function of time at the excimer wavelength of 470 nm using a recorder. For example, a decrease of 10% in the fluorescence intensity in 10 minutes means that 100 μl of a sample contains phospholipase $A_2$ enough to hydrolyze 10% of the total phospholipid content, i.e. about 0.1 nM = 100 μM phospholipid in 10 minutes, and thus the activity of the sample corresponds to 100 μM liberated fatty acid/minute and ml.

By changing the sensitivity level of the fluorometer it is possible to measure the degree of hydrolyzis in samples the activity of which varies between 1 nM and 100 μM free fatty acid/minute and ml. When the results were compared with the results obtained by using a radioactive substrate, the result shown in FIG. 1 was obtained, from which it can be seen that the results obtained with both methods are uniform.

EXAMPLE 2

The lipase activity was measured using the following lipid substrate
1.00 ml of a solution containing
50 μl olive oil
5 μl ethanol (=0.5%)
1 μg 1-oleoyl-2-(4-(3-pyrenyl)-buturyl)-3-oleoyl-si-glycerol
5 mM Na-deoxycholate
50 mM tris-HCl, pH 8.4.

The fluorescence was measured using a fluorescence spectrofotometer connected to a recorder, excitation opening 20 nm, emission opening 20 nm, excitation wavelength 343 nm. Emission was folled at the wavelength 400 nm. First the base level was measured whereafter 50 μl of a sample containing lipase was added and the increase in fluorescence intensity per time unit was followed at the monomer wavelength of ca 400 nm.

In the appended FIG. 2 is shown an assay with normal and pathological serum. The fluorescence intensity Im was measured at the monomer wavelength 400 nm as a function of time. As fluorescent compound the above 1-oleoyl-2-(4-(3-pyrenyl)-buturyl-3-oleoyl-sn-glycerol was used. Benzene boronate was used for stopping the reaction.

Example 2 may be repeated but using as an intramolecularly quenched compound 1 μg of 1-(6-bromohexanoyl)-2-(4-(3-pyrenyl)-buturyl)-3-oleoyl-sn-glycerol and measuring the increase in fluorescence intensity per time unit, as above.

Instead of an intramolecularly quenched compound one can use in the same assaying system 1 μg of 1-oleoyl-2-(4-(3-pyrenyl)-buturyl)-3-oleoyl-sn-glycerol together with 1 μg of 1-oleoyl-2-(6-bromohexanoyl)-3-oleoyl-sn-glycerol, which in oil forms an intramolecularly quenched macromolecule. The increase in fluorescence intensity per time unit after the addition of enzyme is measured as above.

EXAMPLE 3

The phospholipase $A_2$ activity was measured using a substrate which in 2.0 ml contains
0.5 mM $CaCl_2$
0.1 mM egglecithin
0.25 mM Na-deoxycholate
0.2 mM cholate
0.1% (w/vol) bovine serum albumin
50 mM tris-HCl, pH 7.0
40 μg of fluorescent phospholipid.

As phospholipids the following compounds may be used:
(a) 1-(4-(3-pyrenyl)-buturyl)-2-(6-bromohexanoyl)-sn-glycero-3-phosphorylglycerol
(b) 1-(4-(3-pyrenyl)-buturyl) -2-(6-bromohexanoyl)-sn-glycero-phosphorylethylenglycol
(c) 1-(hexatriacontanyl)-2-(4-(3-pyrenyl)-buturyl) -sn-glycero-3-phosphorylglycerol
(d) 1-(6-bromohexanoyl)-2-(4-(3-pyrenyl)-buturyl)-sn-glycero-3-phosphorylcholine
(e) 1-(4-(2-anthryl)-buturyl)-2-(6-bromohexanoyl)-sn-glycero-3-phosphorylglycerol
(f) 1-(10-(2-anthryl)-decanoyl)-2-(10-(3,5-dibromo-4-methoxyphenyl)-decanoyl)-sn-glycero-3-phosphorylglycerol
(g) 1-(10-(2-anthryl)decanoyl)-3-linoleyl-sn-glycerol-2-phosphorylcholine
(h) 1-(10-(3-pyrenyl)-decanoyl)-3-(12-bromododecanoyl)-sn-glycerol-2-phosphorylcholine The lecithin and the fluorescent compound were dried solvent free in a nitrogen stream. Thereafter the Na-deoxycholate was added and the mixture sonicated using a Branson sonifier equipped with microtip at setting 4. Thereafter the bovine serum albumin was added, dissolved in buffer. The substrate was stable for several day provided 0.1 mM $NaN_3$ was added to prevent microbial growth.

To 2.0 ml of substrate 200 μl of serum is added. After mixing, the solution is transferred to a cuvette. Stirring is not necessary when emulsified substrates are used.

Fluorescence changes were measured using a Kontron SFM-23 spectrofluorometer equipped with a magnetically stirred cell (1.0×1.0×0.5 cm). Temperature was controlled with a cryostat at 37° C. throughout the measurement. The fluorescence intensity signal was fed into a recorder. Excitation wavelength was 343 nm for the pyrenyl containing compounds and 370 nm for the anthryl containing compounds, and the changes in the monomer fluorescence intensity were followed 400 nm for pyrenyl and at 450 nm for anthryl.

EXAMPLE 4

The lipase activity was measured using a substrate which in 2.0 ml contains

| | |
|---|---|
| 0.005 mM tributyrin | |
| 0.15 M NaCl | |
| 0.03% (vol./vol.) Span 80 | detergents |
| 0.01% Tween 80 | |
| 50 mM tris-HCl, pH 8.4 | |
| 4.35 μg of fluorescent acylglycerol | |

(a) 1-(4-(3-pyrenyl)-buturyl) -2-(6-bromohexanoyl)-3-oleoyl-sn-glycerol
(b) 1-(4-(3-anthryl)-buturyl) -2-(6-bromohexanoyl)-3-oleoyl-sn-glycerol
(c) 1-(4-(3-pyrenyl)-buturyl)-2-(6-bromohexanoyl)-sn-glycerol.

The lipid to be tested was dried in a stream of nitrogen whereafter the tributyrin and detergents were added, as well as the buffer solution, whereafter the mixture was sonified as in Example 3. In case the sample a was to be stored 0.1 mM of $NaN_3$ was added to prevent microbial growth. The substrate was stable for several days. The solution is to be thoroughly stirred prior to use.

To this solution 200 μl of serum was added, whereafter the mixture was transferred to a cuvette and the change in fluorescence intensity measured as stated in Example 3.

EXAMPLE 5

Preparation of 1,2-di (3-pyrene-4-buturyl)-sn-glycerol-phosphonyl-3-sn-glycerol

D-mannitol-3,4-benzeneboronate-solution

D-mannitol (4.55 g) and benzene boronic acid anhydride (2.65 g) was dissolved in 75 ml of pyridine. 25 ml of cyclohexane was added. The cyclohexane-water-azeotrope was distilled off. 20 ml of pyridine and 5 g of 4 Å molecular sieves were added.

1,2,5,6-tetra(3-pyrene-4-buturyl)-D-mannitol

Four milliliter (1 mmole) of D-mannitol-3,4-benzeneboronate-solution was cooled to −18° C. 1.3 g of 3-pyrene-4-buturyl-chloride was added in 12 ml of trichloroethylene. The mixture a was left standing over night at −18° C. and at room temperature for 4 hours. The reaction mixture was washed with 24 ml of 2-M hydrochloric acid and with water. The mixture was fractionated in a column containing 40 g of Sephadex LH-20 eluting with chloroform-90% ethanol, 1:1-mixture, whereby the boronic acid protection was removed. Yield 0.92 g (73%).

1,2-di(3-pyrene-4-buturyl)-sn-glycerol 0.13 g of periodic acid was dissolved in 3 ml of i-propanol. This solution was added to a mixture containing 0.63 g of 1,2,5,6-tetra(3-pyrene-4-buturyl)-D-mannitol in 6 ml of trichloroethylene. After half an hour the mixture was washed with water until neutral. The solvent was evaporated in vacuum. The residue was dissolved in 10 ml of ethylacetate and reduced with 38 mg of sodium borohydride dissolved in 1 ml of water. After two hours the reaction mixture was washed with 10 ml of 0.1N hydrochloric acid and with water until neutral. The mixture was evaporated to dryness and the residue dissolved in a small amount of a 1:1-mixture of chloroform-90% ethanol. It was fractionated on a column containing 40 g of Sephadex LH-20 using as eluent a 1:1-mixture of chloroform-90% ethanol. Yield 0.38 g (60%).

1,2-di(3-pyrene-4-buturyl)-sn-glycerol-phosphoryl-3-sn-glycerol

While cooling on an ice bath 153 mg of phosphorousoxychloride and 101 mg of triethylamine in 2 ml of trichloroethylene were mixed. 0.32 g of 1,2-di(3-pyrene-4-buturyl)-sn-glycerol was added. After half an hour 334 mg of 1-trityl-sn-glycerol and 202 mg of triethylamine in 4 ml of trichloroethylene was added. The mixture was left standing over night at room temperature. 10 ml of 0.1-M hydrochloric acid was added and the mixture vigorously stirred for four hours. 10 ml of methanol and 10 ml water was added. The water phase was separated. The washing was repeated until the pH of the washing water was 4. The mixture was fractionated on a silicium acid column containing 10% boric acid. It was eluted with chloroform-methanol-mixtures. Yield 0.17 g (49%).

What is claimed is:

1. Method of fluorometrically measuring the activity of fat-degrading enzymes in samples containing said enzyme, characterized in that the sample containing said enzyme is combined with a substrate which in the form of oil or fat emulsion droplets, micelles or liposomes contains a compound having the formula

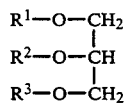

wherein (a) at least two of the groups $R^1$, $R^2$ and $R^3$ denotes a saturated or unsaturated acyl group with 3 to 36 carbon atoms, and the third of these can denote also hydrogen or a saturated or unsaturated alkyl group with 3 to 36 carbon atoms, or (b) one of the groups $R^2$ and $R^3$ denotes a phosphoryl group

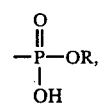

wherein R is hydrogen, ethanolamine, ethylene glycol, choline, glycerol or serine, and the other, as well as $R^1$, denotes an acyl or alkyl group as defined above, provided, however, that the carbon atom in 2-position to the phosphoryl group may contain only an acyl group, and wherein in the compound of formula I, always at least one of the acyl or alkyl groups $R^1$, $R^2$ and $R^3$ is substituted with a fluorescent group, and one or both other groups may be optionally substituted with a fluorescence quenching group, said compound being one that reacts with the enzyme to be assayed, the substrate is excited at the specific excitation wavelength of the fluorescent group in question and the change, due to the enzyme, in the fluorscence intensity of the substrate per time unit is measured at a specific emission wavelength of the fluorescent group, the rate of change being directly proportional to the enzyme activity in the sample.

2. Method according to claim 1, characterized in that as a fluorescent group pyrene is used, whereby the substrate is excited at a wavelength of about 320 to 345 nm, and the rate of change of the fluorescence intensity is measured at either the monomer wavelength of pyrene of about 390 to 400 nm or at its excimer wavelength of about 470 nm.

3. Method according to the claims 1 or 2, characterized in that the fluorescence quencher is a halogen selected from the group consisting of bromine, iodine and chlorine.

4. Method according to the claims 1 or 2, characterized in that when using a compound containing two fluorescent groups, the fluorescence is sensitized by introducing into one of the groups electron donating groups and into the other electron attracting groups.

5. Method according to claim 1, characterized in that as a compound of formula I 1-oleoyl-2-(4-(3-pyrenyl)-buturyl)-3-oleoyl-sn-glycerol is used.

6. Method according to claim 1, characterized in that as a compound of formula I 1,2-di-(4-(3-pyrenyl)-buturyl)-sn-glycero-sn-3-phosphorylglycerol is used.

* * * * *